United States Patent [19]

Mehta et al.

[11] 4,091,100
[45] May 23, 1978

[54] SULFIDE COMPOUNDS

[75] Inventors: Nariman Bomanshaw Mehta; Lawrence Edward Brieaddy, both of Raleigh, N.C.

[73] Assignee: Burroughs Wellcome Co., Research Triangle Park, N.C.

[21] Appl. No.: 726,007

[22] Filed: Sep. 23, 1976

Related U.S. Application Data

[62] Division of Ser. No. 597,697, Jul. 21, 1975, Pat. No. 3,997,540.

[51] Int. Cl.$^2$ .................. C07D 295/08; A61K 31/495
[52] U.S. Cl. .................................... 424/250; 544/401
[58] Field of Search ...................... 260/268 R; 424/250

[56] References Cited

FOREIGN PATENT DOCUMENTS 2,070,081   9/1971   France.
1,305,488   1/1973   United Kingdom.

Primary Examiner—Donald G. Daus
Assistant Examiner—Jose Tovar
Attorney, Agent, or Firm—Donald Brown

[57] ABSTRACT

Compounds, pharmaceutical preparations containing same, and method of treating depression in mammals, the compounds being of the formula I

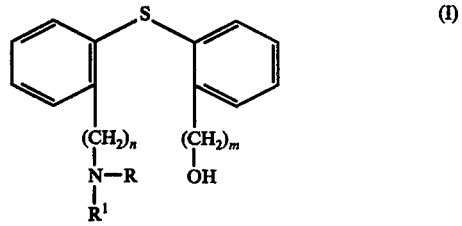

or an acid addition salt thereof, particularly a pharmacologically or pharmaceutically acceptable salt thereof, where R and $R^1$ are the same or different and are each hydrogen or lower alkyl, or R and $R^1$ taken together are $(CH_2)_X$ where X is 4 or 5, or $NRR^1$ is

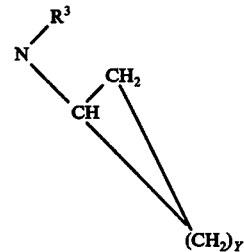

where Y is 3 or 4 and $R^3$ is hydrogen or lower alkyl, or $NRR^1$ is

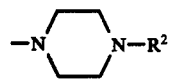

where $R^2$ is hydrogen or lower alkyl, in the above lower alkyl has 1 to 4 carbons and may be straight or branched and $n$ and $m$ are the same or different and are 1, 2, or 3.

18 Claims, No Drawings

SULFIDE COMPOUNDS

This is a division, of application Ser. No. 597,697 filed July 21, 1975, U.S. Pat. No. 3,977,540 granted 12/19/76.

The present invention relates to substituted diphenyl sulfides which are useful in the treatment of mammals such as mice, dogs, rats or humans (man) suffering from a depressed state or condition.

In particular the present invention is directed to compounds represented by the formula I

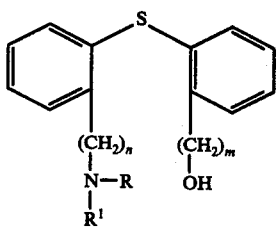

or an acid addition salt thereof where R and $R^1$ are the same or different and are each hydrogen or lower alkyl or R and $R^1$ taken together are $(CH_2)_X$ where X is 4 or 5 or $NRR^1$ is

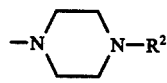

where $R^2$ is hydrogen or lower alkyl or $NRR^1$ is

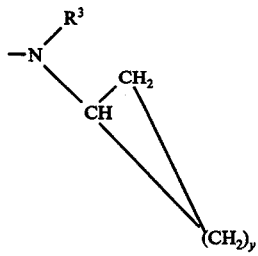

where Y is 3 or 4 and $R^3$ is hydrogen or lower alkyl, in the above lower alkyl has 1 to 4 carbon atoms and may be straight or branched and n and m are the same or different and are each 1, 2 or 3.

Of the compounds of formula I those which are preferred are those in which $NRR^1$ are the same or different and are hydrogen or lower alkyl of 1 to 4 carbons. The most preferred of formula I are those in which $NRR^1$ are the same or different and are hydrogen or lower alkyl of 1 to 4 carbons and n and m=1.

In particular the salts should be pharmaceutically acceptable acid addition salts when used for administration to a mammal. However it should be understood that toxic salts may conveniently be converted to pharmaceutically acceptable salts in a conventional exchange reaction, double decomposition reaction or by other known methods.

In addition acid addition salts e.g. toxic and non-toxic (i.e. pharmaceutically acceptable salts) are useful in the preparation of useful compounds known in the art. The compounds of formula I possess valuable properties as antidepressants when tested by standard techniques used in the art for determining antidepressant activity, for example the tetrabenzene-induced sedation test in the rat. The compounds of this invention are also notable for their low toxicity. Of the compounds of formula I the following is especially preferred for its high antidepressant activity.

2-N,N-Dimethylaminomethyl-2'-hydroxymethyl-diphenyl sulfide m.p. 161°–163° C. Other compounds of notable activity are as follows:

2-N-Methylaminomethyl-2'-hydroxymethyldiphenyl sulfide m.p. 217°–219° C.

2-Aminomethyl-2'-hydroxymethyldiphenyl sulfide m.p. 188°–190° C.

2-N,N-Diethylaminomethyl-2'-hydroxymethyldiphenyl sulfide m.p. 148°–150° C.

2-N-Ethylaminomethyl-2'-hydroxymethyldiphenyl sulfide m.p. 182°–183° C.

Other compounds of particular interest include those of formula I which are as follows:

| $NRR^1$ (where n=m=1) | |
|---|---|
| $N(CH_2)_4$ | m.p. 190–192° C |
| $N(CH_2)_5$ | m.p. 172–173° C |
| ⌐N⌐N—CH₃ (piperazinyl) | m.p. 243–244° C |

In the above m.p.=melting point

The compounds of this invention may be synthesized by any of a number of methods which may be classified in terms of the final step as follows:

(a) Formation of sulfide bridge [Methods (1) and (2)].

(b) Reduction of —$CO_2H$(Alk) to —$CH_2OH$ and/or -CONRR' to —$CH_2NRR'$ [Methods (3)-(7) and (15)].

(c) Replacement of a leaving group on one of the methylene substituents by OH or NRR' [Methods (8) and (9)].

(d) Alkylation of the —NHR [Methods (10)–(12)].

(e) Reduction of a sulfone (—$SO_2$—) or sulfoxide (-SO-) bridge to a sulfide (-S-) bridge [Method (13)].

(f) Reduction of

when neither R nor $R^1$ is hydrogen [Method (14)].

Abbreviations used herein: Alk is lower alkyl; LAH is lithium aluminum hydride; DMA is dimethylacetamide; DMF is dimethylformamide; DMSO is dimethylsulfoxide; red. is reducing agent.

The above classifications may be exemplified by the following methods:

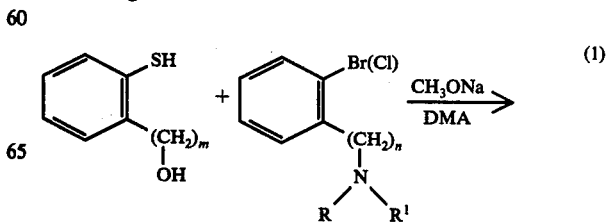

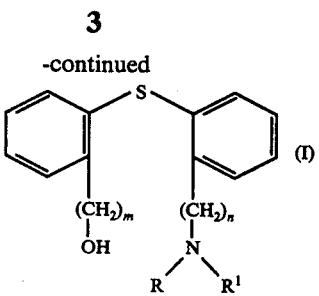 (I)

Reaction conditions: Anhydrous; suitable reaction temperature about room temperature to about the boiling point of the solvent; other suitable solvents include DMF and DMSO.

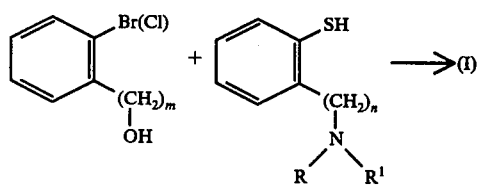 (2)

Reaction conditions: Same as Method (1).

Step (a)

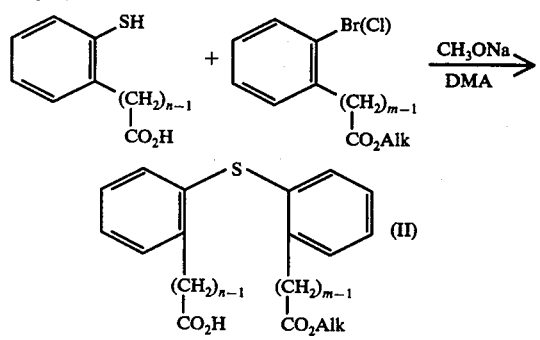 (3)

Reaction conditions: Same as Method (1).

Step (b)

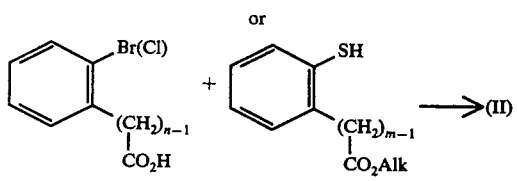

Reaction conditions: May be carried out net (i.e. with excess $SOCl_2$ as solvent) or in a non-reactive solvent such as benzene, toluene, methylene chloride, etc.); temperature about room temperature to the boiling point of the solvent.

Step (c)

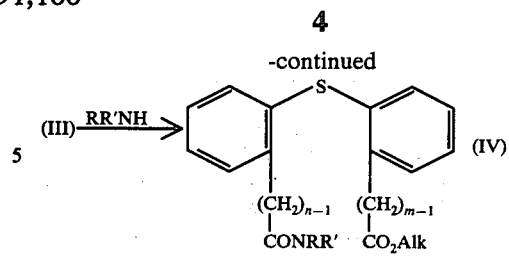 (IV)

Reaction conditions: May be conveniently carried out in aqueous medium using sodium hydroxide to neutralize the hydrogen chloride formed. Organic solvents such as ether, toluene, etc. may be used; alcohol may also be used provided the acid chloride is added to an alcoholic solution of the amine. An excess of the amine or a tertiary amine such as triethylamine may be used to neutralize the hydrogen chloride formed if desired. Temperatures used are generally low, from 0° C to about room temperature but may be higher if desired.

Step (d)

(IV) $\xrightarrow{LAH}$ (I)

Reaction condition: Generally carried out in ether (e.g. diethyl ether or tetrahydrofuran) solution and at room temperature, but slightly elevated temperatures could be used.

Step (a)

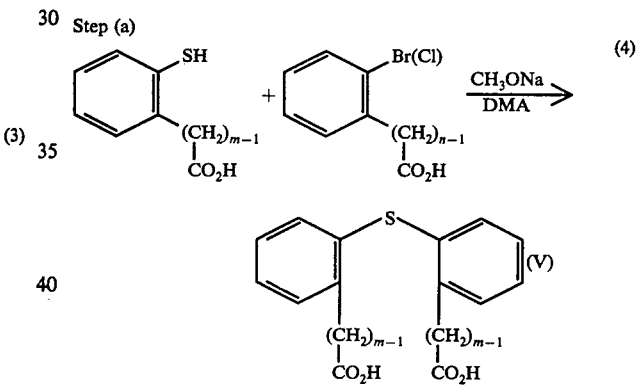 (4)

Reaction conditions: Same as Method (1). May also be carried out in aqueous sodium hydroxide at elevated temperatures. May conveniently be carried out in the presence of copper and potassium carbonate in aqueous medium in a bomb at elevated temperature, e.g. 120° C.

Step (b)

(V) $\xrightarrow{KOH}{AlkOH}$ (II)

Reaction conditions: Anhydrous; equimolar amount of alcohol used; solvents such as dioxane, DMSO suitable.

(II) may be converted into (I) as in steps (b), (c) and (d) of method (3).

Step (a)

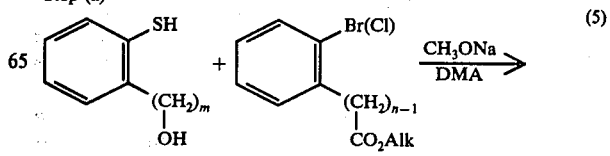 (5)

-continued

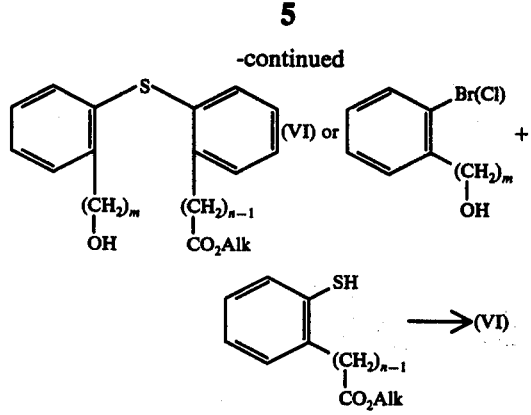

Reaction conditions: Same as Method (1)

Step (b)

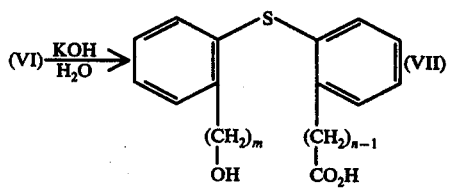

Reaction conditions: Conveniently carried out in aqueous alcohol at elevated temperatures.

Step (c)

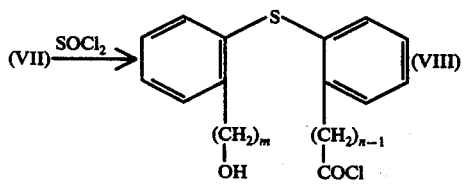

Reaction conditions: Same as Method (3) step (b).

Step (d)

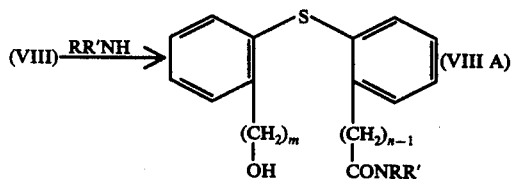

Reaction conditions: Same as Method (3) step (c).

Step (e)

Reaction conditions: Same as Method (3) step (d)

 (6)

Reaction conditions: May be carried out in aqueous or alcoholic solvents at temperatures ranging from about room temperature to reflux. Anhydrous solvents, e.g. xylene, at elevated temperatures may also be used.

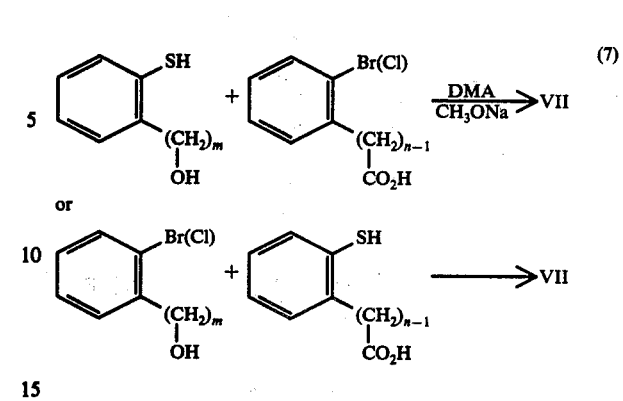

Reaction conditions: Same as Method (1)
(VII) may be converted into (I) as in Method (5) steps (c) ff.

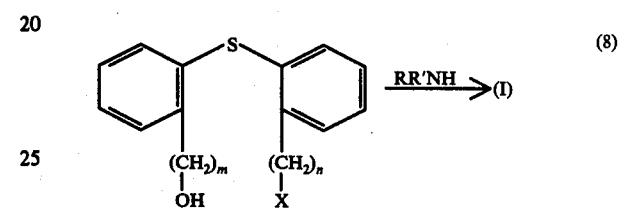

Reaction conditions: X is a leaving group displacable by an amine, such as halide (esp. bromide), tosylate, mesylate, or azide. An inert solvent such as e.g. toluene, dioxane, acetonitrile and temperatures from about room temperature to reflux may be used.

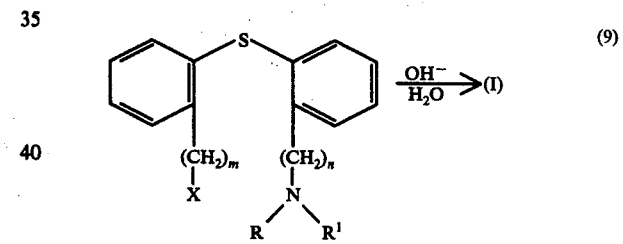

Reaction conditions: X is as defined in Method (8) plus carboxylic esters, dilute alkali in aqueous solution such as e.g. water, acetonitrile, DMF at elevated temperatures are generally used.

Step (a)

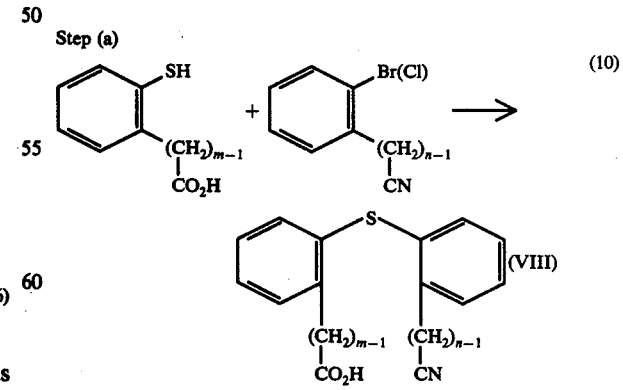

Reaction conditions: Same as Method (1)

Step (b)

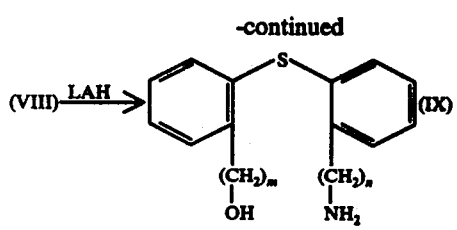

Reaction conditions: Same as Method (3) step (d).

Step (c)

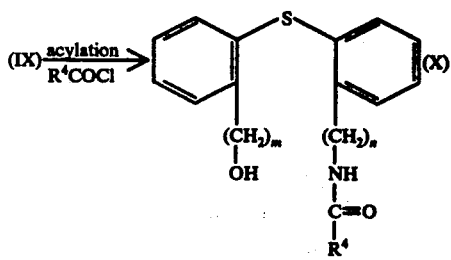

Reaction conditions: Generally same as Method (3) step (c) except that if a base is used to neutralize the hydrochloric acid formed it should be an organic base. $R^4$ is lower alkyl.

Step (d)

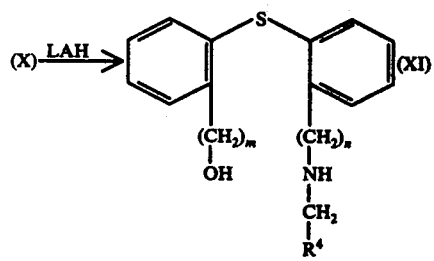

Reaction conditions: Same as Method (3) step (d).

(XI) may be further alkylated by repeating steps (c) and (d) to provide the teriary amino compound.

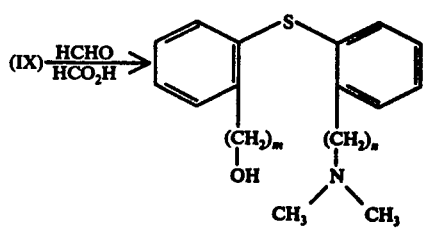

Reaction conditions: Generally carried out in aqueous, alcoholic or polar aprotic solvents such as acetonitrile, DMF, DMSO at elevated temperatures. Other reducing agents (than the formic acid) which may be used include formic acid derivatives such as ammonium formate and metal hydride derivatives such as $NaBH_3CN$.

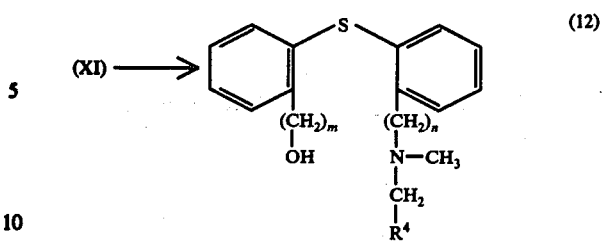

Reaction conditions: Same as Method (11)

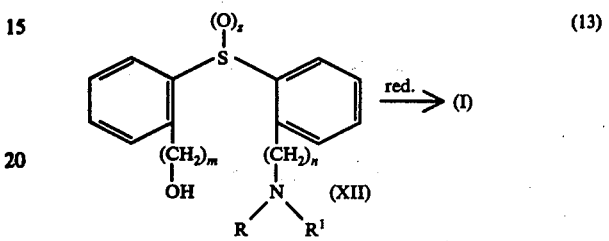

Reaction conditions: Z is 1 or 2, reducing agents such as triphenylphosphine or metal hydride derivatives such as LAH may be used in non-reactive organic solvents such as ethers.

Compounds (XII) may be prepared by oxidizing the diphenyl sulfide intermediates of Method (8) or strong acid addition salts, e.g. hydrochloride salts, of the diphenyl sulfide intermediates of Method (9) by conventional methods (e.g. perbenzoic acid in toluene at room temperataure) followed by the replacement reactions described in these methods.

The diphenylsulfide intermediates of Methods (3)–(7) may be oxidized as above to give the corresponding sulfoxide or sulfone intermediates which may then be carried thru the remaining steps of these methods giving in the final step simultaneous reduction the sulfone or sulfoxide moiety and the amide and/or ester (or acid) moieties.

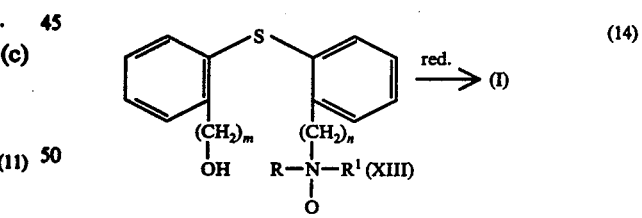

Reaction conditions: Reducing agents and solvents as in Method (13) are suitable.

The compounds (XIII) may be prepared by oxidation of the diphenylsulfide intermediates of Method (9) with e.g. $NaIO_4$.

Similarly, compounds having both sulfoxide (or sulfone) and N-oxide moieties may be prepared by nonspecific oxidation (e.g. using m-chloroperbenzoic acid in toluene at room or elevated temperature) of the intermediates of Method (a). These may be converted into compounds of formula (I) by replacing the leaving group with OH as in Method (9) and then simultaneously reducing the sulfoxide (sulfone) and N-oxide groups using reaction conditions as in Method (13).

Step (A)

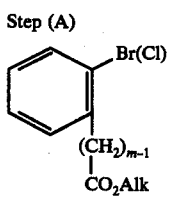
+
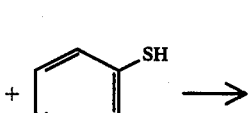
→

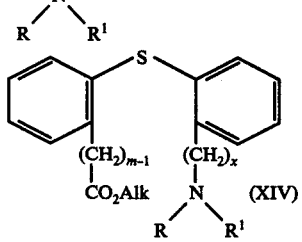 (XIV)

Reaction conditions: Same as Method (1)

Step (b)

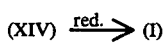

Reaction conditions: Same as Method (3) step (d).

The preferred antidepressant dosage for parenteral administration of a compound of formula (I) (estimated as the base) is about 5 mg/kg to 50 mg/kg of mammal body weight, and the most preferred dosage being 15 mg/kg to 35 mg/kg of mammal body weight.

For the oral or rectal mode of administration, the preferred antidepressant dosage of a compound of formula (I) (estimated as the base) is about 10 mg/kg to 100 mg/kg of mammal body weight while the most preferred dosage (estimated as the base) is about 30 mg/kg to 70 mg/kg of mammal body weight. A compound of formula (I), or an acid addition salt thereof, is preferably administered four times daily although the number of daily administrations of the medication may vary according to the patient (mammal) being treated, and the exercise of the physician's discretion.

For the treatment of depression in humans, the preferred unit dosage of a compound of formula (I) or an acid addition salt thereof (as the base) for oral administration, or administration as a suppository, is about 15 milligrams to 500 milligrams with the more preferred unit dosage being about 100 milligrams to 300 milligrams, and the most preferred unit dosage being about 125 milligrams to 250 milligrams. All the above doses are given in terms of the weight of a compound of formula (I) in the form of its base, but as will be appreciated from the foregoing information, it is preferably administered in the form of a pharmaceutically acceptable acid addition salt thereof.

A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel, or merely the capsule shell as well as other excipients well known in the art for this purpose.

According to the present invention there is provided a compound of the formula (I) and a pharmaceutically acceptable salt thereof.

According to the present invention, in yet another aspect, there is provided a pharmaceutical composition (preferably in unit dosage form) comprising a compound of formula (I) (or a pharmaceutically acceptable salt thereof) together with a pharmaceutically acceptable carrier. Conveniently the compound of formula (I) or its acid addition salt comprises from 5 to 95% by weight of the composition.

According to the present invention in yet another aspect there are provided methods of synthesizing compounds of formula (I) comprising the application of methods specified above those apparent therefrom for the preparation of diphenyl sulphide of formula I.

According to still a further aspect of the present invention, there is provided a method of treating a depressed state in mammals such as humans, mice, rats, dogs, etc., which comprises the administration of an antidepressant effective non-toxic amount (dose), preferably in a unit dosage form, of a compound of formula (I) or a pharamaceutically acceptable salt thereof.

The compounds of formula (I) (the active ingredients) or the pharmaceutically acceptable salt thereof is preferably administered in unit dosage form to the mammal being treated.

The compounds of this invention may be administered orally, parenterally or rectally.

A pharmaceutical composition containing a compound of formula (I), or a pharmaceutically acceptable salt thereof, may be presented in discrete units such as tablets, capsules, ampoules or suppositories, each containing an effective antidepressant non-toxic amount of the compound.

A compound of formula (I) or a pharmaceutically acceptable salt thereof may be presented for rectal use as a suppository with the usual pharmaceutically acceptable carries such as cocoa butter, and may be presented for parenteral use as an ampoule of a sterile solution or suspension with water or other pharmaceutically acceptable liquid as the carrier therefor, or as an ampoule of a sterile powder for dilution with a pharmaceutically acceptable liquid.

It should be understood that in addition to the aforementioned ingredients, the pharmaceutical compositions of this invention may include one or more of additional ingredients such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

The compound of formula I is preferably represented for use in the treatment of depressed states as a pharmaceutically accetable salt. Examples of some of the pharmaceutically acceptable salts which can be utilized are salts of the following inorganic or organic acids: hydrochloric, sulfuric, phosphoric, toluenesulphonic, maleic, fumaric, tartaric, citric, acetic, pamoic, and succinic.

Acid addition salts may also be formed from acids such as nitric and oxalic.

In addition the compounds of this invention where R and $R^1$ in formula I are the same or different and each is lower alkyl or hydrogen and n=m=1 are useful as intermediates in the preparation of compounds of the general formula of U.S. Pat. No. 3,803,143 by treating same with $PBr_3$ in chloroform at room temperature.

For example where R is H and $R^1$ is lower alkyl, the compounds are directly converted to the compounds of U.S. Pat. No. 3,803,143.

2-Hydroxymethyl-2'-methylaminomethyldiphenyl sulfide was treated with $PBr_3$ in chloroform at room temperature and 6-N-methyl-5H,7H-dibenzo[b,g]-

(1,5)thiazocine was obtained (Example 20 U.S. Pat. No. 3,803,143).

Where R and $R^1$ are hydrogen, the same procedure may be followed and the amine is then alkylated by formaldehyde/formic acid as is conventional.

Where R and $R^1$ are both lower alkyl, a quaternary salt is formed and thereafter one of the alkyls is displaced by hydride e.g. lithium aluminum hydride in a conventional manner.

The present invention is also directed to intermediates of the formula A and B which are converted as disclosed herein to the compounds I.

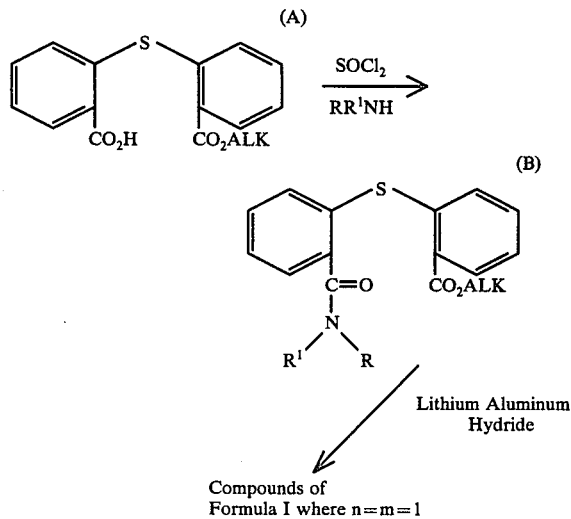

In the above ALK is lower alkyl of 1 to 4 carbons and R and $R^1$ are as defined in Formula I. In particular ALK is preferably ethyl.

The following examples illustrate the invention. All temperatures are in degrees C.

EXAMPLE 1

2-Carbethoxy-2'-carboxydiphenyl sulfide 2,2'-Dicarbethoxydiphenyl sulfide (120 g.) was added to a solution of potassium hydroxide (22 g.) in one liter of ethanol and stirred at room temperature for 4 days. It was acidified with concentrated hydrochloric acid, filtered. The product obtained on concentration of the filtrate to dryness was partitioned between ether and five percent sodium bicarbonate. The mixture of diacid and half ester-acid obtained on acidification was triturated with warm benzene to separate the insoluble diacid. The product was precipitated by the addition of n-hexane to the benzene extract. Recrystallization from acetone/n-hexane mixtures gave 2-carboxy-2'-carbethoxydiphenyl sulfide (43.0 g., 37%), m.p. = 122° – 23° C.

EXAMPLE 2

2-Carbethoxy-2'-dimethylaminocarbonyldiphenyl sulfide

The half ester-acid chloride (32.0 g.) obtained by the reaction of 2-carbethoxy-2'-carboxydiphenyl sulfide (30.2 g.) with excess thionyl chloride was dissolved in 150 ml. of dry dioxane and added to an excess of ice-cold solution of dimethylamine in dry dioxane. The solution was stirred at room temperature for 1 hour, acidified, filtered. The residue obtained by concentrating the filtrate in vacuo was dissolved in 250 ml. of chloroform and washed successively with 10% acid, 5% bicarbonate and water. On drying and subsequent removal of the solvent, 32.0 g. (97%) of the amide-ester was obtained as an orange colored oil.

EXAMPLES 3 AND 4

The following were prepared by the procedure of Example 2.

2-Carbethoxy-2'-aminocarbonyldiphenyl sulfide m.p. = 126°–29° C (80% yield)

2-Carbethoxy-2'-methylaminocarbonylidiphenyl sulfide m.p. = 92°–94° C (96% yield)

EXAMPLE 5

2-Hydroxymethyl-2'-dimethylaminomethyldiphenyl sulfide .HCl

To a slurry of lithium aluminum hydride (15.2 g) in 800 ml. of tetrahydrofuran, at room temperature, was added a solution of 2-carbethoxy-2'-dimethylaminocarbonyldiphenyl sulfide 32.9 g. in 150 ml of tetrahydrofuran and the mixture was stirred at room temperature for 18 hours. The reaction was worked up in the usual manner and the free base was obtained as a yellow oil. The hydrochloride salt was crystallized from ethanol/ether mixtures to give 19.0 g. (60% yield) of 2-hydroxymethyl-2'-dimethylaminomethyldiphenyl sulfide, m.p. 162°–64° C.

EXAMPLES 6 AND 7

The following were prepared by the procedures of Examples 2 and 5.

2-Hydroxymethyl-2'-aminomethyldiphenyl sulfide .HCl m.p. = 188°–89° C (60% yield)

2-Hydroxymethyl-2'-methylaminomethyldiphenyl sulfide .HCl M.P. = 218°–20° C (90% yield)

EXAMPLE 8

2,2'-Dicarboxy diphenyl sulfide

2-Bromobenzoic acid (40.0 g.) and 2-mercaptobenzoic acid (32.0 g) were dissolved in 140 ml of water, containing 56 g. of potassium carbonate. Upon dissolution, 13.0 g of powdered Cu was added. This homogeneous solution was transferred to a stainless steel bomb and heated at 130°–140° for 3 hr. Bomb was cooled; contents were filtered and the filtrate acidified with conc. HCl. Filtration yielded 52.8 g (97%) of 2,2'-dicarboxydiphenyl sulfide, m.p. 225°–30° C [Lit. m.p. 233°, C. A. 54, 9815d (1960)].

EXAMPLE 9

2,2'-Dicarbethoxydiphenyl sulfide 2,2'-Dicarboxydiphenyl sulfide (54.8 g., 0.20 mol.) was treated with excess thionyl chloride (100 ml.) at 60° C until a clear solution was obtained. The excess thionyl chloride was removed under reduced pressure. The resulting solid was then treated with 200 ml. of EtOH at reflux for 30 min. The ethanol solution was added to 1 liter of ice water. The diester was filtered and dried, yielding 62.0 g (90%), m.p. 56°–57° [lit. m.p. 58°–59°, C. A. 54, 9815d (1960)].

EXAMPLE 10

2-Carbethoxy-2'-N-methylpiperazinocarbonyldiphenyl sulfide

To the solution of 3.6 g. of 2-carbethoxy-2'-chlorocarbonyldiphenyl sulfide in 100 ml. of acetonitrile, at room temperature, was added a solution of 11.6 g. of N-methylpiperazine in 50 ml. of triethylamine. After 3 hours of stirring the solvent was removed and the residue was taken up in 250 ml chloroform. It was washed successively with 10% hydrochloric acid, sodium bicarbonte and water. On concentration 13.0 g. (94% yield) of an orange oil was obtained.

EXAMPLE 11

2-Hydroxymethyl-2'-N-methylpiperazinomethyldiphenyl sulfide .HCl

To a slurry of 4.0 g. of lithium aluminum hydride in 500 ml. of tetrahydrofuran, at room temperature, was added a solution of 12.6 g. of 2-carbethoxy-2'-N-methylpierazinocarbonyldiphenyl sulfide iin 100 ml. of tetrahydrofuran. The mixture was stirred at room temperature for 18 hours. The reaction was worked up in the usual manner to afford 9.2 g. (85%) of the free base as a yellow oil. The hydrochloride salt was crystallized from 50% aqueous EtOH to afford 9.0 g. (65%) of the product as a dihydrate, m.p. 243°–44° C.

EXAMPLE 12

2-Carbethoxy-2'-pyrrolidinocarbonyldiphenyl sulfide

To the stirred solution, at room temperature, of 4.8 g. of pyrrolidine in 50 ml. of triethylamine was added 20 g. of 2-carbethoxy-2'-chlorocarbonyl diphenyl sulfide in 150 ml. of dry acetonitrile. After stirring for 3 hours the solvents were removed in vacuo and the residue taken up in 250 ml. of chloroform. It was successively treated with 10% hydrochloric acid, 5% bicarbonate and water. After drying, concentration and recrystallization from acetone-hexane mixtures 17.0 g. (72% yield) of pure product, m.p. 117°–19° C, was obtained.

EXAMPLE 13

2-Carbethoxy-2'-piperidinocarbonyldiphenyl sulfide

Following the procedure of Example 12, 2-carbethoxy-2'-piperidinocarbonyldiphenyl sulfide, m.p. 111°–13° C, was prepared in 75% yield.

EXAMPLE 14

To the slurry of 13.3 g. of lithium aluminum hydride in 800 ml. of tetrahydrofuran was added a solution of 25 g. of 2-carbethoxy-2'-pyrrolidinocarbonyldiphenyl sulfide in 150 ml. of tetrahydrofuran under nitrogen atmosphere at room temperature. It was stirred for 18 hours. The reaction mixture was decomposed by the usual procedure and the hydrochloride salt of the base, m.p. 190°–92° C, 17.0 g. (73% yield) was obtained. The compound obtained was 2-hydroxymethyl-2'-pyrrolidinomethyldiphenyl sulfide .HCl

EXAMPLE 15A

2-Hydroxymethyl-2'-piperidinomethyldiphenyl sulfide .HCl M.P. 172°–73° C

Following the procedure of Example 12, 2-hydroxymethyl-2'-piperidinomethyldiphenyl sulfide was prepared in the hydrochloride salt, m.p. 172°–173° C, in 80% yield.

EXAMPLE 15

Tablet Formulation 150 mg. of 2-N,N-Dimethylaminomethyl-2'-hydroxymethyl diphenyl sulfide hydrochloride
85 mg. Lactose
50 mg. Cornstarch
10 mg. Micronized Silica Gel
5 mg. Polyvinyl pyrrolidone
Procedure The lactose, cornstarch and salt is mixed together and granulated with a binder, polyvinyl pyrollidone in alcoholic solution, to form granules. The granules were passed through a 16–20 mesh screen, then air dried, lubricated with micronized silica gel and compressed into tablets. A film coating could then have been applied if desired.

EXAMPLE 16

Capsule Formulation 150 mg. of 2-N-methylaminomethyl-2'-hydroxymethyl diphenyl sulfide hydrochloride is mixed with 125 mg. of lactose and 125 mg. of cornstarch. The mixture was filled into a two piece hard gelatin capsule.

EXAMPLE 17

Parenteral Solution 150 mg. of 2-N,N-diethylaminomethyl-2'-hydroxymethyl diphenyl sulfide hydrochloride is dissolved in sterile water U.S.P. to make 1 ml. A multi-dose preparation may include bacteriostats such a 0.2 to 0.5% w/v of phenol.

EXAMPLE 18

Suppository 150 mg of 2-aminomethyl-240 -hydroxymethyldiphenyl sulfide hydrochloride is mixed with 205 mg. of softened or melted cocoa butter, and suppositories were formed by chilling and shaping in molds.

EXAMPLE 19

Capsule 200 mg. of 2-N-ethylaminomethyl-2'-hydroxymethyl diphenyl sulfide hydrochloride is placed in a two piece hard gelatin capsule.

EXAMPLE 20

Anti-Tetrabenzine Test

Sprague-Dawley male rats weighing approximately 180 gm. were grouped six per cage. Compounds of Formula I as the hydrochloride salt in saline are injected i.p. thirty minutes prior to the administration of tetrabenazine, 20 mg/kg, i.p. Animals were scored according to the method of Sulser and Soroko, Psychopharmacology 8, 191 (1965).

| NRR' where n=m=1 | Effective Anti-Tetrabenzine Activity in the Rat (mg/kg i.p.)* |
|---|---|
| $NH_2$ | 25 |
| $N(CH_3)H$ | 12.5 |
| $N(CH_3)_2$ | 12.5 |
| $N(C_2H_5)_2$ | 25 |

*Equal to a standard desmethylimipramine at 5 mg/kg i.p. similarly injected into rats as above.

EXAMPLE 21

6-Methyl-5H,7H-dibenzo[b,g][1,5]thiazocine

To a solution of 19.6g (0.076 mol) of 2-hydroxymethyl-2'-methylaminomethyldiphenyl sulfide in 1 l. of chloroform was added a solution of 13.5g (0.05 mol) of phosphorus tribromide in 100 ml. of chloroform under an atmosphere of $N_2$ while keeping the reaction vessel immersed in an ice bath. This solution was stirred for 2 hours at ice bath temperatures; then 17 hours at room temperature. This cloudy solution was refluxed for 2 hours, cooled, 500 ml. of ice $H_2O$ added. Potassium carbonate was added until the aqueous phase was alkaline. The organic layer was separated; the basic aqueous layer was extracted three times with 200 ml. portions of chloroform. The chloroform extracts were combined and dried over anhydrous potassium carbonate. Removal of chloroform under reduced pressure gave a yellow oil. This oil was triturated with ether with the simultaneous precipitation of a tan solid, filtered and the ether removed to get 16.9g (92%) of a low melting solid. The amine was converted to its hydrochloride salt via ethereal.HCl. Recrystallization from ethanol-acetone afforded a white solid: m.p. 217°–219°.

What is claimed is:

1. A compound of the formula

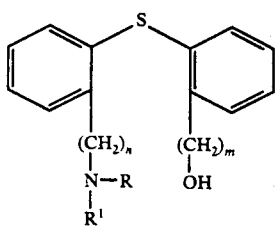

or a pharmaceutically acceptable acid addition salt thereof where $NRR^1$ is

where $R^2$ is hydrogen or lower alkyl of 1 to 4 carbon atoms and $n$ and $m$ are 1.

2. A compound of claim 1 in which $R^2$ is methyl.
3. A pharmaceutical preparation consisting essentially of an effective antidepressant amount of the compound of the formula

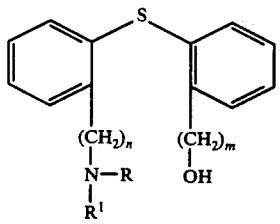

or a pharmaceutically acceptable salt thereof where $NRR^1$ is

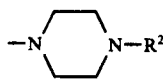

where $R^2$ is hydrogen or lower alkyl of 1 to 4 carbon atoms, $n$ and $m$ are 1.

4. A preparation of claim 3 in which $R^2$ is methyl.
5. A preparation of claim 3 in a form for oral, parenteral or rectal administration.
6. A preparation of claim 3 in unit dosage form.
7. A preparation of claim 3 in which the pharmaceutical preparation is in the form of a tablet, capsule or injectable preparation.
8. A preparation of claim 3 in which the amount is 15 to 500 milligrams.
9. A method of treating depression in a mammal consisting essentially of administering to a depressed mammal an effective antidepressant amount of a compound of the formula

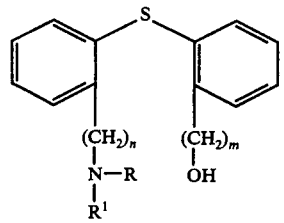

or a pharmaceutically acceptable acid addition salt thereof where $NRR^1$ is

where $R^2$ is hydrogen or lower alkyl of 1 to 4 carbon atoms, and $n$ and $m$ are 1.

10. A method of claim 9 in which $R^2$ is methyl.
11. A method of claim 9 in which the mammal is a human.
12. A method of claim 9 in which the amount is 5 to 100 mg/kg as base.
13. A method of claim 9 in which the compound or salt is administered orally or parenterally.
14. A method of claim 10 in which the amount is 5 to 100 mg/kg as base.
15. The method of claim 10 in which the compound or salt is administered orally or parenterally.
16. A method of claim 10 in which the mammal is a human.
17. The method of claim 13 in which the amount is 5 to 50 mg/kg and the compound is administered parenterally.
18. The method of claim 13 in which the amount is 10 to 100 mg/kg and the compound is administered orally.

* * * * *